United States Patent
Ikeuchi et al.

(10) Patent No.: US 7,713,217 B2
(45) Date of Patent: May 11, 2010

(54) TORQUE IMPARTING SYSTEM

(75) Inventors: Yasushi Ikeuchi, Wako (JP); Hisashi Katoh, Wako (JP); Takashi Hirata, Wako (JP)

(73) Assignee: Honda Giken Kogyo Kabushiki Kaisha, Tokyo (JP)

( * ) Notice: Subject to any disclaimer, the term of this patent is extended or adjusted under 35 U.S.C. 154(b) by 1299 days.

(21) Appl. No.: 10/481,807

(22) PCT Filed: Jun. 27, 2002

(86) PCT No.: PCT/JP02/06468
§ 371 (c)(1),
(2), (4) Date: Dec. 22, 2003

(87) PCT Pub. No.: WO03/002054
PCT Pub. Date: Jan. 9, 2003

(65) Prior Publication Data
US 2004/0158175 A1 Aug. 12, 2004

Related U.S. Application Data

(60) Provisional application No. 60/300,815, filed on Jun. 27, 2001.

(30) Foreign Application Priority Data

Jul. 2, 2001 (JP) .............................. 2001-200416
Aug. 3, 2001 (JP) .............................. 2001-236336

(51) Int. Cl.
| | |
|---|---|
| *A61B 5/103* | (2006.01) |
| *A61B 5/117* | (2006.01) |
| *A61F 2/74* | (2006.01) |
| *A61F 2/60* | (2006.01) |
| *A61F 2/78* | (2006.01) |
| *A61F 2/68* | (2006.01) |
| *A61F 2/62* | (2006.01) |
| *A61F 2/64* | (2006.01) |
| *A61F 2/66* | (2006.01) |
| *A61F 2/54* | (2006.01) |
| *A61F 2/00* | (2006.01) |
| *A61F 2/58* | (2006.01) |

(52) U.S. Cl. .................. 600/595; 600/587; 623/27; 623/30; 623/31; 623/39; 623/40; 623/47; 623/48; 623/49; 623/50; 623/53; 623/57; 623/58; 623/59; 623/60; 623/61; 623/62; 623/63

(58) Field of Classification Search ................. 600/595, 600/587; 623/27, 30, 31, 39, 40, 47–50, 623/53, 57–63
See application file for complete search history.

(56) References Cited

U.S. PATENT DOCUMENTS

| | | | | |
|---|---|---|---|---|
| 5,808,433 | A | * | 9/1998 | Tagami et al. .......... 318/568.12 |
| 5,827,209 | A | | 10/1998 | Gross |
| 2001/0029343 | A1 | * | 10/2001 | Seto et al. ................... 600/587 |

FOREIGN PATENT DOCUMENTS

EP 0 911 015 4/1999

(Continued)

*Primary Examiner*—Max Hindenburg
*Assistant Examiner*—Jeffrey G Hoekstra
(74) *Attorney, Agent, or Firm*—Rankin, Hill & Clark LLP

(57) ABSTRACT

A system for assisting the motion of a body connected through joints provides a system for imparting a suitable torque to the connected body at the time of various turns including the bending of the joints. The torque imparting system has first and second measuring means, a reference work volume determining means, and an external torque determining means. The first measuring means measures the internal work volume of the around-joint leg. The second measuring means measures an external work volume around a joint imparted to the leg. The reference work volume determining means determines a reference work volume based on the internal work volume. The external torque determining means determines an external torque imparted to the leg so as to reduce the difference between the internal work volume of the leg and the reference work volume, based on the external work volume.

29 Claims, 6 Drawing Sheets

FOREIGN PATENT DOCUMENTS

| | | |
|---|---|---|
| JP | 7-163607 A | 6/1995 |
| JP | 09271496 | 10/1997 |
| JP | 11-300661 | 11/1999 |
| JP | 2000-107213 A | 4/2000 |
| JP | 2000-166997 | 6/2000 |

* cited by examiner

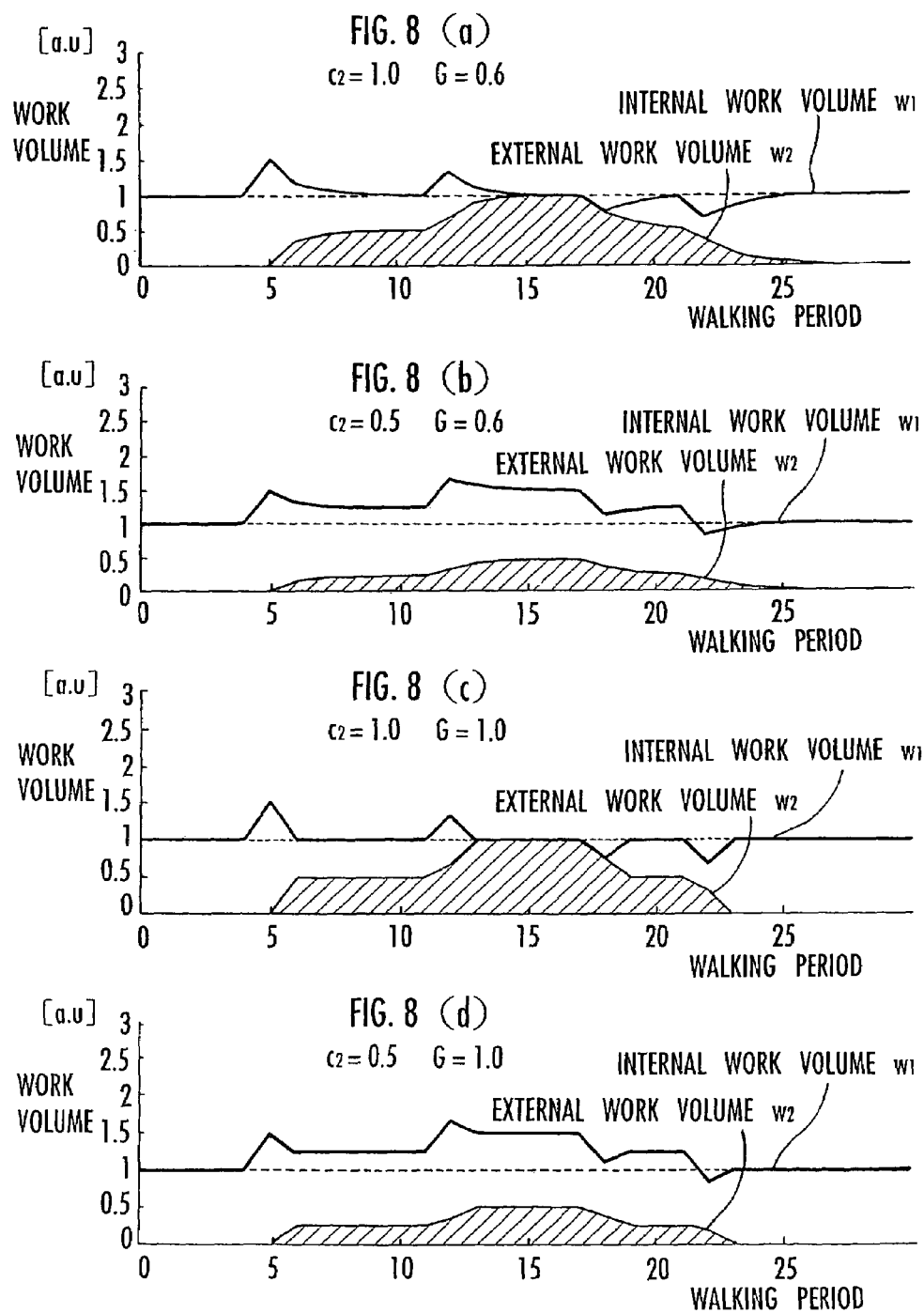

US 7,713,217 B2

TORQUE IMPARTING SYSTEM

TECHNICAL FIELD

The present invention relates to a system for imparting an external torque around a joint with respect to a connected body relatively rotatably connected through joints, more particularly to a system for imparting the external torque around a foot joint, knee joint, or hip joint with respect to a walker's leg.

BACKGROUND ART

A system for assisting walking of a person who has difficulty in walking without help because of a drop of strength in legs has been proposed in Japanese Patent Application Laid-Open Nos. 7-163607 and 2000-166997, and the like. In this system, a torque imparting apparatus is attached to patient's knee joint portions and the like, a torque is imparted to knees by the apparatus, and this assists a walker in walking.

However, according to a conventional system, walking conditions on stairs, flatland, and the like are only roughly identified, and the torque has been imparted without identifying various walking conditions such as stairs including irregular steps and slops having different inclinations. Therefore, there is a possibility that the imparted torque becomes excessive.

Therefore, a problem to be solved by the present invention is to provide a system that is capable of imparting a suitable torque to a connected body in accordance with motional situations of the connected body at the time of various turns including the bending of joints, through a construction of the system capable of suitably assisting the motion of the connected body connected, in general, through joints, to a leg body of the walker, in accordance with to various motional conditions of the connected body.

DISCLOSURE OF THE INVENTION

To solve the problem, according to the present invention, there is provided a torque imparting system including: a first measuring means for measuring an internal work volume around a joint generated from a connected body; a second measuring means for measuring an external work volume around the joint imparted to the connected body; a reference work volume determining means for determining a reference work volume on the basis of the internal work volume of the connected body measured by the first measuring means; an external torque determining means for determining an external torque imparted to the connected body in such a manner as to reduce a difference between the internal work volume of the connected body measured by the first measuring means and the reference work volume determined by the reference work volume determining means on the basis of the external work volume measured by the second measuring means; and an external torque imparting means for imparting the external torque determined by the external torque determining means to the connected body.

According to the present invention, the external torque around the joint is imparted to the connected body so that the internal work volume around the joint of the connected body agrees with the reference work volume. Therefore, when motional conditions of the connected body fluctuate, and the work volume of the connected body required for the motion exceeds the reference work volume, the external torque is imparted to the connected body in the form of assistance of a surplus. Moreover, when the internal torque is exerted in accordance with the reference work volume in the connected body regardless of the fluctuation of the motional conditions, the motion can be achieved.

Moreover, the external torque imparted to the connected body is determined on the basis of the external work volume imparted to the connected body, and the reference work volume which is the basis of the determination is determined on the basis of the internal work volume of the connected body. Therefore, a suitable external torque can be imparted to the connected body in accordance with a balance between the internal work volume and the external work volume of the connected body. It is to be noted that the external torque imparted by the present system includes an external torque in all planes such as an xy plane, yz plane, and zx plane assuming that a motion direction is an x-axis and a vertical direction is a z-axis, that is, an external torque in any direction in a three-dimensional space.

Moreover, the torque imparting system of the present invention is characterized in that the connected body is a walker's leg body including a hip joint, knee joint, and foot joint.

According to the present invention, when the suitable torque is imparted in accordance with walking situations on various walking conditions such as the bending of the walker's knee joint of the leg body, the walking can suitably be assisted.

Furthermore, the torque imparting system of the present invention includes a first coefficient determining means for regarding a ratio of the external work volume imparted to the connected body with respect to the internal work volume of the connected body as a desired value in a case in which a difference from the reference work volume determined by the reference work volume determining means is 0 and for successively determining a first coefficient so that the coefficient converges to the desired value with an elapse of time. The first measuring means measures the internal torque around the joint of the connected body, the external torque determining means calculates a product of the internal torque of the connected body measured by the first measuring means and the first coefficient determined by the first coefficient determining means, and the calculation result is determined as the external torque imparted to the connected body.

According to the present invention, when the internal work volume of the connected body exceeds the reference work volume, the first coefficient and further the external torque to be imparted to the connected body are successively determined so as to eliminate the surplus. Moreover, when the first coefficient converges to the desired value, and the external torque determined on the basis of the first coefficient is imparted to the connected body, the motion by the internal torque exerted in accordance with the reference work volume of the connected body can be achieved.

Furthermore, when a convergence rate of the first coefficient to the desired value is increased, and accordingly the work volume required for the motion exceeds the reference work volume by the fluctuation of the motional conditions, the external torque can be imparted to the connected body so as to quickly eliminate the surplus. On the other hand, when the convergence rate of the first coefficient to the desired value is decreased, and accordingly the work volume required for the motion exceeds the reference work volume by the fluctuation of the motional conditions, the external torque can be imparted to the connected body so as to slowly eliminate the surplus.

Moreover, the torque imparting system of the present invention is characterized in that the first coefficient determining means determines an upper limit or a lower limit of the first coefficient on the basis of the internal work volume measured by the first measuring means or the external work volume measured by the second measuring means.

According to the present invention, since the upper limit or the lower limit is set to the first coefficient, a situation where the external torque imparted to the connected body becomes excessively large or small can be avoided. Therefore, when the connected body is the walker's leg body, the walker can walk more comfortably. The upper limit or the lower limit of the first coefficient is determined on the basis of the internal work volume or the external work volume which fluctuates in accordance with a motional situation of the connected body. Therefore, the external torque can suitably be limited in accordance with the motional situation.

Furthermore, the torque imparting system of the present invention is characterized in that the first coefficient determining means determines the lower limit of the first coefficient as 0, when a total work volume constituting a sum of the internal work volume determined by the first measuring means and the external work volume measured by the second measuring means is not more than the reference work volume determined by the reference work volume determining means.

The desired value of the first coefficient is determined so that the internal work volume of the connected body agrees with the reference work volume as described above. Therefore, when the total work volume of the connected body decreases and becomes smaller than the reference work volume, the first coefficient is determined to be negative so that the internal torque of the connected body and further the internal work volume are increased to agree with a reference torque, and a negative external torque constituting a resistance of the motion can be imparted to the connected body.

According to the present invention, in this case, the lower limit of the first coefficient is determined as 0, and the external torque which is determined as a product of the first coefficient and the internal torque is 0. Therefore, a situation where the negative external torque is imparted to the connected body can be prevented.

Moreover, the torque imparting system of the present invention is characterized in that the first coefficient determining means determines the upper limit of the first coefficient, when the total work volume constituting the sum of the internal work volume determined by the first measuring means and the external work volume measured by the second measuring means is not less than a predetermined volume not less than the reference work volume determined by the reference work volume determining means.

When the total work volume of the connected body increases and largely exceeds the reference work volume, the first coefficient can be determined to be excessively large so that the internal torque of the connected body and further the internal work volume are decreased to agree with the reference work volume, and the excessively large external torque can be imparted to the connected body.

According to the present invention, in this case, since the upper limit of the first coefficient is determined, the upper limit is disposed in the external torque determined as the product of the first coefficient and the internal torque. This can prevent a situation where the excessively large external torque is imparted to the connected body.

Furthermore, in the torque imparting system of the present invention, the first measuring means measures a product of the internal torque of the connected body around the joint and an angular velocity thereof, and the first coefficient determining means segments and determines the first coefficient in accordance with a segment of the product measured by the first measuring means. The external torque determining means uses the first coefficient previously determined on the basis of the internal work volume in accordance with the past segment of the product by the first coefficient determining means to determine the external torque, when the segment of the product measured by the first measuring means agrees with the past segment of the product previously measured by the first measuring means.

Moreover, the torque imparting system of the present invention is characterized in that the first coefficient determining means segments and determines the first coefficient depending on whether the product of the internal torque of the connected body around the joint measured by the first measuring means and the angular velocity is positive or negative.

Furthermore, in the torque imparting system of the present invention, the reference work volume determining means calculates the total work volume which is the sum of the internal work volume measured by the first measuring means and the external work volume measured by the second measuring means. The means calculates a product of a difference between the total work volume and the internal work volume of the connected body in a non-load state measured by the first measuring means, and a second coefficient concerning the external torque assuming that the difference between the internal work volume of the connected body and the reference work volume is 0, and calculates a difference between the total work volume and the product to determine the calculation result as the reference work volume.

According to the present invention, for a fluctuation of the total work volume required at the time of the motion with respect to the reference work volume, a fluctuation to be compensated by the external torque is determined by a size of the second coefficient. That is, when the second coefficient is set to be large, a ratio of the fluctuation to be compensated by the external torque in the fluctuation can be increased. On the other hand, when the second coefficient is set to be small, the ratio of the fluctuation to be compensated by the external torque in the fluctuation can be reduced. It is to be noted that "the internal work volume of the connected body in the non-load state" includes: the internal work volume at the time of the motion of the connected body in a state where no load is added from the outside; and also the internal work volume at the time of the motion of the connected body in a state where the load is added from the outside, corrected in consideration of the load so that the internal work volume in the state in which the load is not added can fictitiously be obtained.

Moreover, the torque imparting system of the present invention is characterized in that the first and second measuring means regard a motion period of the connected body as an integration time to measure the internal and external work volumes.

According to the present invention, the external torque to be imparted to the connected body in the next motion period can be determined on the basis of the internal work volume and the external work volume of the connected body in an immediately previous motion period. When the connected body is the walker's leg body, the external torque to be next imparted to the left/right leg body can be determined on the basis of the internal work volume and the external work volume from when the right or left foot leaves a floor until the foot contacts the floor and from when the left or right foot leaves the floor until the foot contacts the floor.

Furthermore, in the torque imparting system of the present invention, the first measuring means measures a reaction force which works on one joint of the connected body, measures a total torque of the internal torque and external torque of the connected body around each joint in accordance with an inverse kinetic model on the basis of measured reaction force, and calculates a difference from the external torque measured by the second measuring means from the measured total torque to measure the internal torque of the connected body around each joint.

Although details are described later, according to the inverse kinetic model, the connected body is assumed as a plurality of rigid rods rotatably and successively connected through the joints, and a torque of one rigid body around another joint and the reaction force of the other joint are determined on the basis of the torque of one rigid rod around one joint and the reaction force of one joint. Therefore, according to the present invention, since the torque around the joint at an end of the connected body and the reaction force of the joint are measured on the basis of the reaction force in the end of the connected body, the torque of the other joint can successively be measured. Moreover, the torque measured in accordance with the inverse kinetic model is the sum of the internal torque and external torque. Therefore, when the external torque is subtracted from the measured torque, the internal torque can be measured.

BRIEF DESCRIPTION OF THE DRAWINGS

FIGS. 7 and 8 are explanatory views of a simulation result of the walking assistance by the walking assisting apparatus.

BEST MODE FOR CARRYING OUT THE INVENTION

An embodiment of a torque imparting system of the present invention will be described with reference to the drawings.

Figure 1:
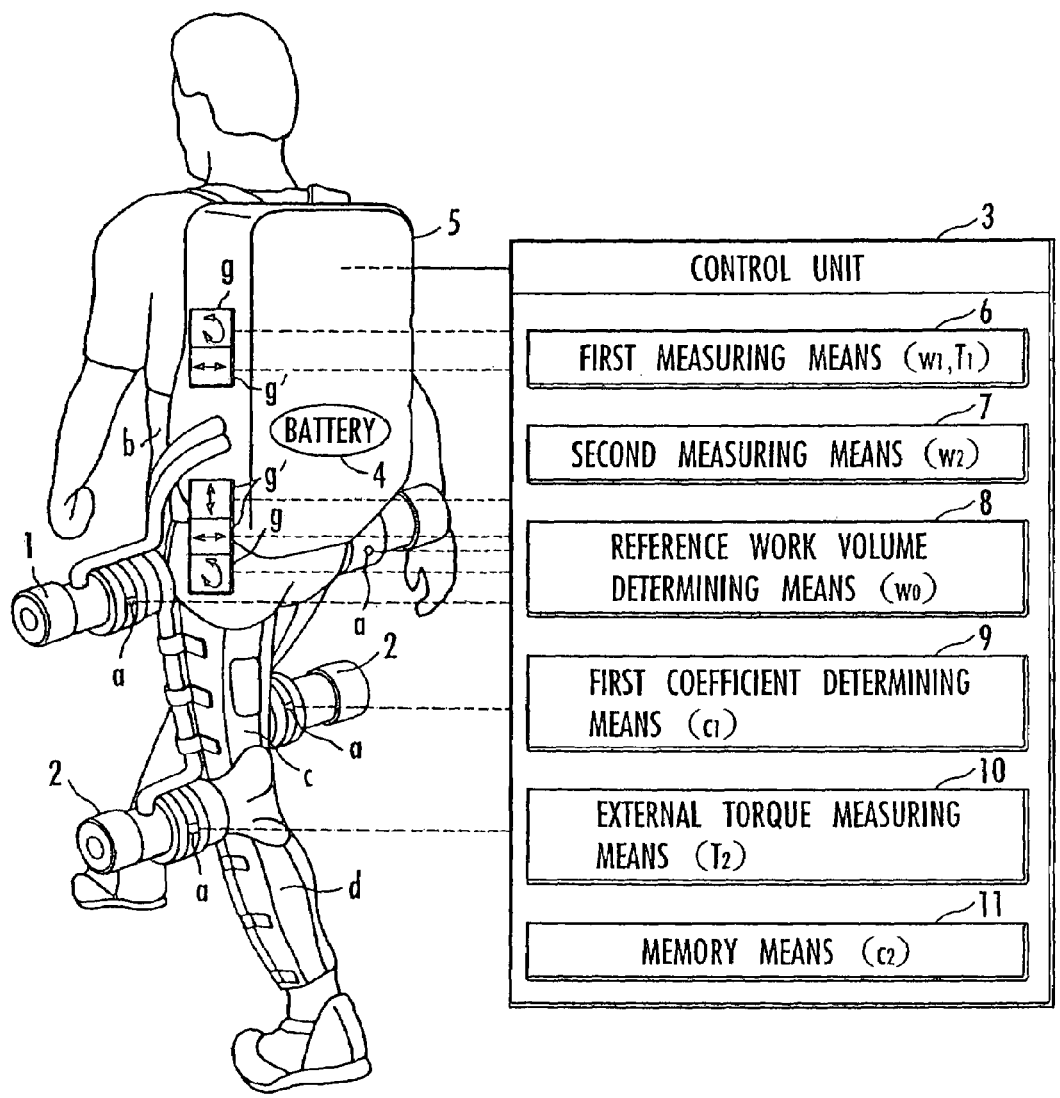
FIG. 1 is a constitutional explanatory view of a walking assisting apparatus which is a torque imparting system of the present embodiment.

The torque imparting system shown in FIG. 1 includes: a first actuator (external torque imparting means) 1, attached to a walker's waist, for imparting an external torque around a hip joint; second actuators (the same as above) 2, attached to walker's knees, for imparting the external torque around a knee joint; a control unit 3 for controlling operations and the like of the respective actuators 1, 2; and a battery 4 such as an Ni—Zn battery for supplying power to the respective actuators 1, 2. The control unit 3 and battery 4 are housed in a backpack 5 carried on a walker's back. The first actuator 1 applies the external torque around the hip joint via a bellyband b and a thigh pad c attached to a walker. The second actuator 2 imparts the external torque around the knee joint via the thigh pad c and shin guard d attached to the walker. It is to be noted that the walker's waist, thigh, and shin correspond to a "connected body".

Moreover, the present walking assisting apparatus is attached to the walker's back, and includes a gyro sensor g for measuring an angular velocity with respect to a vertical direction of the upper part of the body, and a G sensor g' for measuring acceleration in a horizontal direction. The apparatus is further attached to the walker's waist, and includes the gyro sensor g for measuring the angular velocity with respect to the vertical direction of the waist, and the G sensor g' for measuring the acceleration in the horizontal and vertical direction. Moreover, the apparatus includes angle sensors a which are attached to the walker's waist to measure rotation angles of left/right thighs around the hip joints with respect to the waist and which are attached to the knees to measure the rotation angles of the shins with respect to the thighs.

The control unit 3 includes a first measuring means 6, second measuring means 7, reference work volume determining means 8, first coefficient determining means 9, external torque determining means 10, and memory means 11. The control unit 3 is constituted from a combination of CPU, signal input/output circuit, memory, and the like so as to be capable of fulfilling various functions described later.

The first measuring means 6 measures an internal torque $T_1$ of a leg body around knee and hip joints, and an internal work volume $w_1$ which is time integration of an absolute value of a product of the internal torque $T_1$ and an internal angular velocity $\omega_1$ on the basis of measured values of the respective sensors g, g', a. The second measuring means 7 measures an external work volume $w_2$ which is the time integration of the absolute value of the product of an external torque $T_2$ around the knee and hip joints and an external angular velocity $\omega_2$ on the basis of torque values of the respective actuators 1, 2 and the measured values of the angle sensors a. The reference work volume determining means 8 determines a reference work volume $w_0$ on the basis of the internal work volume $w_1$ of the leg body measured by the first measuring means 6. The first coefficient determining means 9 determines a ratio of the external work volume $w_2$ to the internal work volume $w_1$ in a case where a deviation of the internal work volume $w_1$ from the reference work volume $w_0$ determined by the reference work volume determining means 8 becomes 0 as a desired value $c_{TG}$, determines a ratio of the external work volume $w_2$ to the internal work volume $w_1$ as a first coefficient $c_1$ and successively determines the first coefficient $c_1$ so that the coefficient converges to the desired value with an elapse of time. The external torque determining means 10 calculates a product of the internal torque $T_1$ measured by the first measuring means 6 and the first coefficient $c_1$ determined by the first coefficient determining means 9 to determine the external torque $T_2$ imparted around the hip and knee joints through the actuators 1, 2. The memory means 11 is constituted of nonvolatile memories such as ROM, volatile memories such as RAM, and the like, and stores a second coefficient $c_2$ for use in determining the reference work volume $w_0$ as described later, a data table for use in measuring floor reaction forces onto the walker's left/right feet, and the like.

A function of the walking assisting apparatus constituted as described above will be described with reference to FIGS. 2 to 8.

Figure 2:
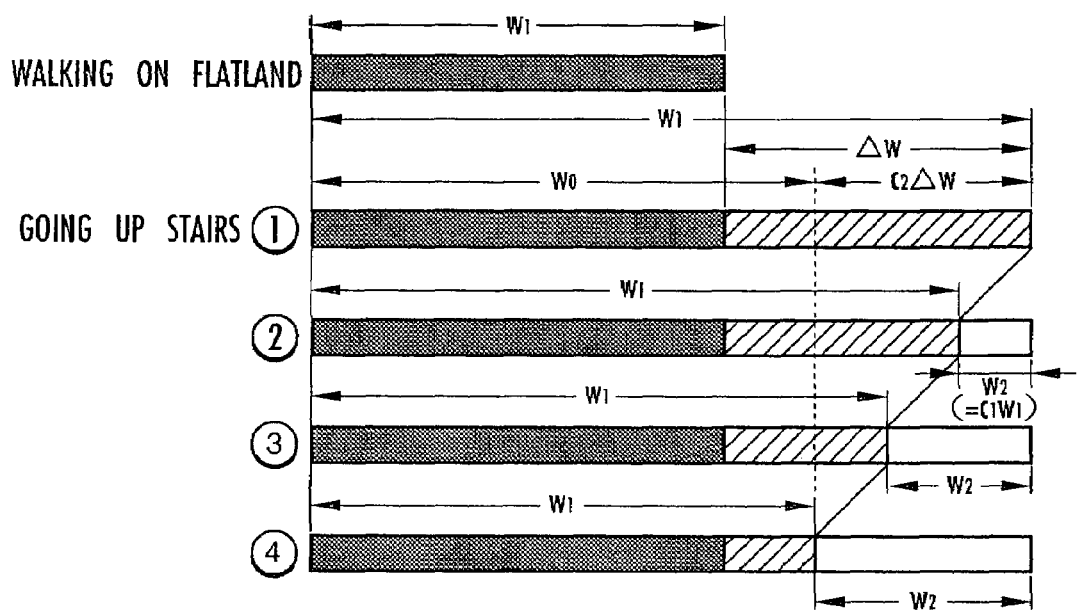
FIG. 2 is a schematic explanatory view of walking assistance by the walking assisting apparatus.

First, an outline of the external torque around the knee joint imparted to the walker's leg body from the second actuator 2 will be described with reference to FIG. 2. The internal work volume $w_1$ around the knee joint at the time when the walker walks on a flatland in a non-load state is shown in blackened portions. It is to be noted that the "internal work volume $w_1$ in the non-load state" includes: an internal work volume measured by a three-dimensional motion analysis apparatus and the like in a state in which the walking assisting apparatus is not attached to the walker; and also an internal work volume determined by decreasing the internal work volume measured by the angle sensors a in a state in which the walking assisting apparatus is attached to the walker in consideration of a weight or friction of the apparatus.

It is assumed that the internal work volume $w_1$ around the knee joint exceeds that at the time of the walking on the flatland by $\Delta w$ (see shaded portions of FIG. 2 ①), when the walker starts going up the stairs. This exceeding is caused because the walker needs to move the leg body more largely in going up the stairs than in walking on the flatland. Therefore, the walker who can walk on the flatland but cannot walk up the stairs because of a drop in muscle strength has difficulty in going up the stairs.

To solve the problem, the external torque $T_2$ is imparted to the leg body so as to assist the walker in walking up the stairs. After determining the reference work volume w as described later, the external torque $T_2$ is successively determined on the basis of the internal torque $T_1$ so that the internal work volume $w_1$ converges to this reference work volume $w_0$. Accordingly, as the walker goes up the stairs, the external work volume $w_2$ (see whitened portions of FIG. 2 ② to ④) gradually increases every shift to ② from ①, ③ from ②, ④ from ③ in FIG. 2, and accordingly the internal work volume $w_1$ gradually decreases to converge to the reference work volume $w_0$. Therefore, a burden on the walker's muscle strength required for generating the internal torque around the knee joint is decreased as the walker goes up the stairs. Thereafter, the walker can continue walking up the stairs by the internal torque $T_1$ exerted in accordance with the reference work volume $w_0$.

Next, details of a procedure for determining the external torque $T_2$ around the hip and knee joints imparted to the leg body from the first and second actuators 1, 2 will be described with reference to FIGS. 3 to 6. It is to be noted that affix i is suitably attached to a physical amount in a walker's i-th (i=1, 2, . . . ) walking period (hereinafter referred to as the "i-th period").

Figure 3:
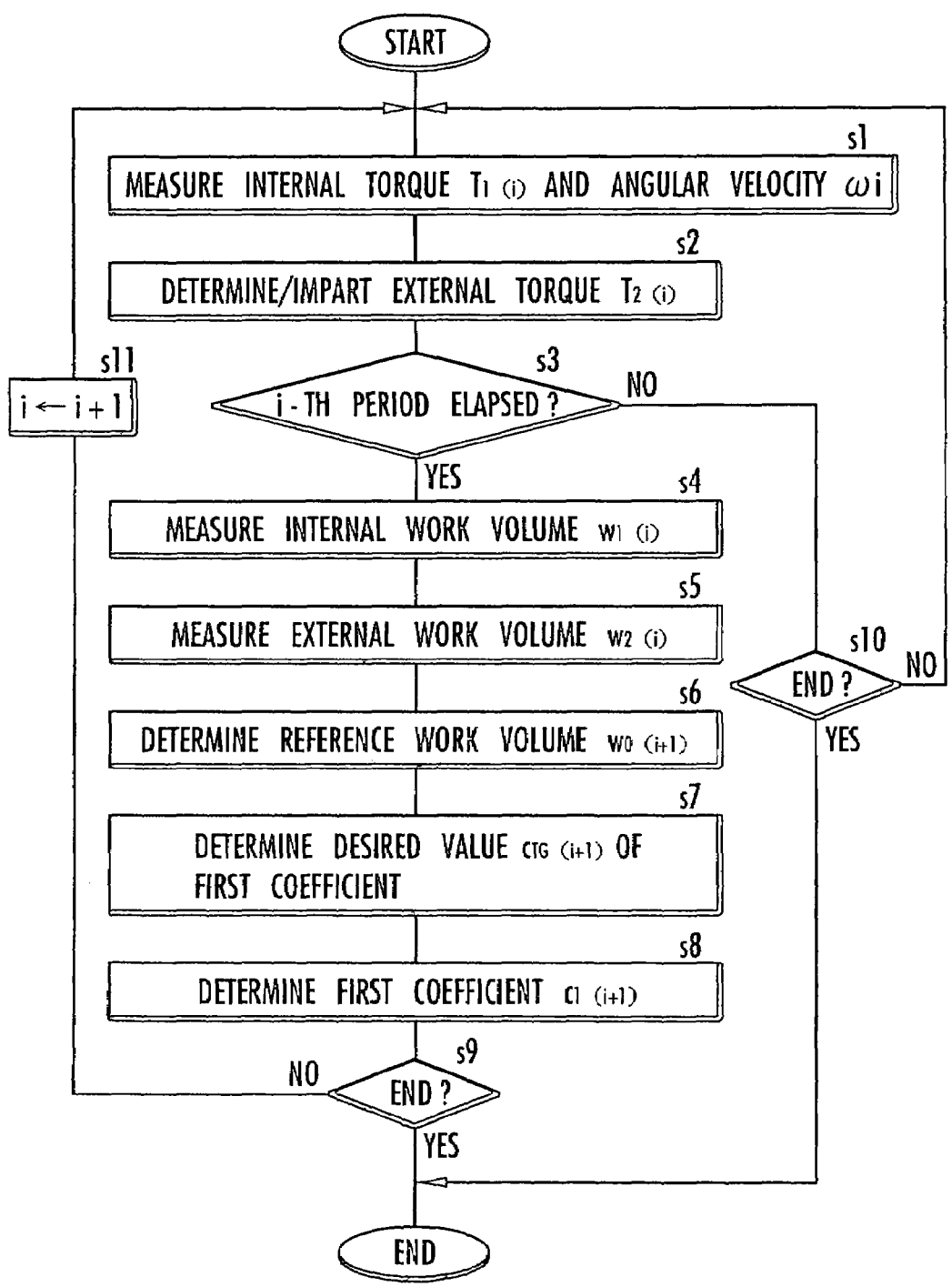
FIG. 3 is a flowchart showing a function of the walking assisting apparatus.

First, the internal torque $T_{1(i)}$ and angular velocity $\omega_{1(i)}$ around the knee and hip joints are measured (FIG. 3 s1). A method of measuring the internal torque $T_{1(i)}$ will be described with reference to FIGS. 4 and 5.

Figure 4:
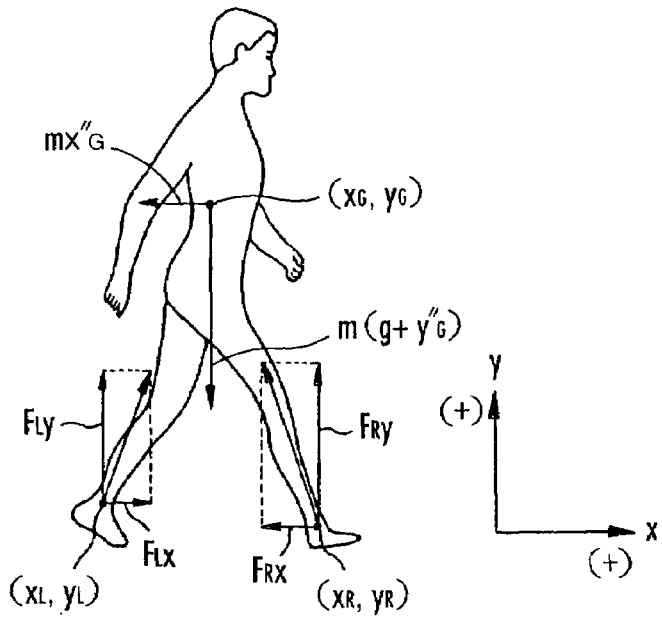
FIG. 4 is a schematic explanatory view of floor reaction force measurement of a walker's foot.

The floor reaction forces onto the walker's left/right leg bodies are measured using a model shown in FIG. 4. Floor reaction forces $(F_{Lx}, F_{Ly})$, $(F_{Rx}, F_{Ry})$ act on the left and right leg bodies of the walker having a mass m shown in FIG. 4. Walker's body gravity center coordinate, left foot joint coordinate, and right foot joint coordinate are $(x_G, y_G)$, $(x_L, y_L)$, $(x_R, y_R)$, respectively. In consideration of a balance or direction of the force in this model, the following relational equations (1a) to (1d) are obtained.

$$F_{Ry}+F_{Ly}=m(g+y_G'') \text{ (g: gravity acceleration)} \quad (1a)$$

$$F_{Rx}+F_{Lx}=mx_G'' \quad (1b)$$

$$(y_G-y_R)/(x_G-x_R)=F_{Ry}/F_{Rx} \quad (1c)$$

$$(y_G-y_L)/(x_G-x_L)=F_{Ly}/F_{Lx} \quad (1d)$$

The walker's mass m is measured beforehand. The body gravity center coordinate $(x_G, y_G)$, left/right foot joint coordinates $(x_L, y_L)$, $(x_R, y_R)$, and accelerations $(x_G'', y_G'')$ of the body gravity center coordinate are measured on the basis of the measured values of physical measurement of the walker in advance, gyro sensor g and G sensor g' attached to the walker's waist and the like, and angle sensors a attached to the hip and knee joints. In detail, the left/right foot joint coordinates $(x_L, y_L)$, $(x_R, y_R)$, and the like are measured on the basis of a data table in which correspondences with the angles of the hip or knee joints, the lengths of the thigh and shin, and the like stored in the memory means 11 are specified. Moreover, when these measured values are assigned to the above relational equations, the first measuring means 6 measures the floor reaction forces $(F_{Lx}, F_{Ly})$, $(F_{Rx}, F_{Ry})$.

Figure 5:
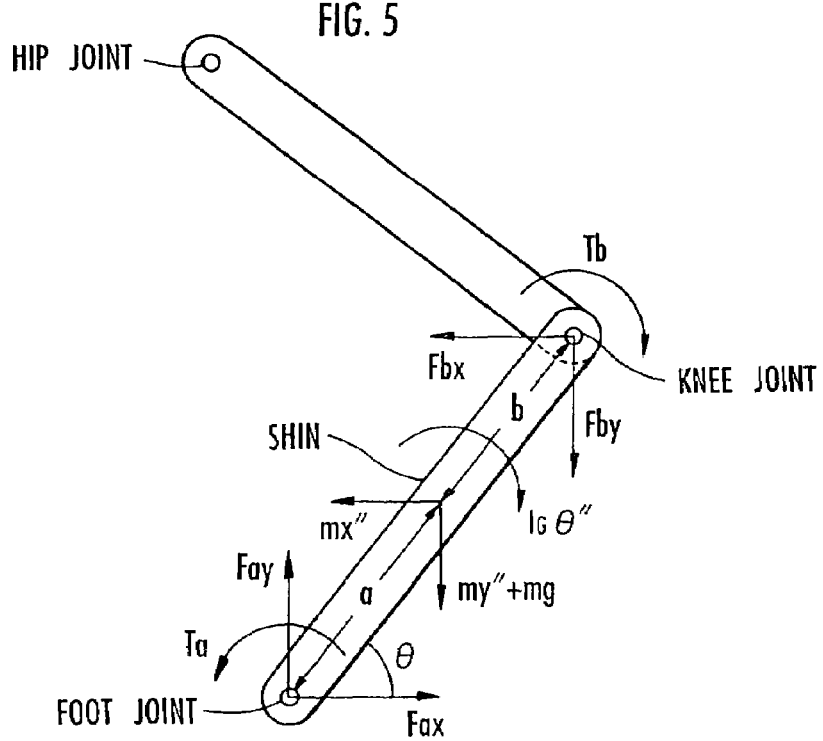
FIG. 5 is a schematic explanatory view of torque measurement around a walker's joint.

Next, a total torque around the knee and hip joints is measured in accordance with an inverse kinetic model using a model shown in FIG. 5 based on the measured floor reaction force. As shown in FIG. 5, it is assumed that a floor reaction force $(F_{ax}, F_{ay})$ acts on the foot joint, a reaction force $(F_{bx}, F_{by})$ acts on the knee joints, and a force $(mx'', m(y''+g))$ accompanied by the acceleration acts on the center of gravity of the shin with the mass m. It is also assumed that torques around the foot and knee joints are $T_a$, $T_b$, respectively, an angle formed between the shin and the floor is $\theta$, moment of inertia of the shin is I, and distances between the foot and knee joints and the center of gravity of the shin are a, b, respectively. In consideration of the balance of the force or torque in this model, the following relational equations (2a) to (2c) are obtained.

$$F_{ax}-F_{bx}-mx''=0 \quad (2a)$$

$$F_{ay}-F_{by}-my''-mg=0 \quad (2b)$$

$$I\theta''=T_a-T_b+F_{ax}a\sin\theta-F_{ay}a\cos\theta+F_{bx}b\sin\theta-F_{by}b\cos\theta \quad (2c)$$

The floor reaction force $(F_{ax}, F_{ay})$ is measured by the above-described method. Moreover, an acceleration $(x'', y'')$ of the center of gravity of the shin, angle $\theta$ of the shin with respect to the floor, and angular acceleration $\theta''$ are measured on the basis of the measured values of the physical measurement of the walker in advance and the gyro sensor g, G sensor g', and angle sensors a attached to the walker. Furthermore, the moment of inertia of the shin I, and the distances a, b between the foot and knee joints and the center of gravity of the shin, respectively, are measured on the basis of the physical measurement of the walker in advance. The torque $T_a$ around the foot joint is measured by the first measuring means 6 in accordance with the data table stored in the memory means 11 on the basis of the floor reaction force $(F_{ax}, F_{ay})$. Moreover, when these measured values are assigned to the above relational equations (2a) to (2c), the torque $T_b$ around the knee joint is measured. Similarly, the above relational equations (2a) to (2c) are also used to measure the torque around the hip joint.

When an external torque $T_{2(i)}$ imparted by the first and second actuators 1, 2 is subtracted from the torque around the knee and hip joints measured as described above, the internal torque $T_{1(i)}$ around the knee and hip joint is measured (FIG. 3 s1). The internal angular velocity $\omega_{1(i)}$ and external angular velocity $\omega_{2(i)}$ (since both are considered to substantially agree with each other, they are represented by an angular velocity $\omega_{(i)}$ in common) are also measured by the angle sensors a (FIG. 3 s1). It is to be noted that the external torque $T_{2(i)}$ around each joint is measured by the second measuring means on the basis of the torque values of the first and second actuators 1, 2.

Next, the external torque $T_{2(i)}$ is determined by the external torque determining means 10, and imparted to the walker's leg body through the first and second actuators 1, 2 (FIG. 3 s2). The external torque $T_{2(i)}$ is determined by the product of the internal torque $T_{1(i)}$ successively measured by the first measuring means 6 and a first coefficient $c_{1(i)}$ determined by the first coefficient determining means 9 every walking period. That is, the first coefficient $c_{1(i)}$ determines the percentage of the external torque $T_{2(i)}$ with respect to the internal torque $T_{1(i)}$. A method of determining the first coefficient $c_{1(i)}$ will be described later.

Subsequently, the control unit 3 judges whether or not an i-th period has been elapsed (FIG. 3 s3). Specifically, a period in which the floor reaction force of the right foot measured by the first control means 6 turns to 0 from a finite value, again turns to the finite value, and thereafter turns to 0 is judged as an elapse of a walking period.

The above-described process of s1 to s3 is repeated before the elapse of the i-th period (NO in s3 of FIG. 3) and until the operation of the walking assisting apparatus is ended.

When it is judged that the i-th period has elapsed (YES in s3 of FIG. 3), the first measuring means 6 measures the internal work volume $w_{1(i)}$ around each joint is measured in accordance with the next equation (3) (FIG. 3 s4). That is, the internal work volume $w_{1(i)}$ is measured by integrating the absolute value of the product of the internal torque $T_{1(i)}$ around each joint and the angular velocity $\omega_{(i)}$ over the i-th period.

$$w_{1(i)} = \int dt \cdot |T_{1(i)} \times \omega_{(i)}| \tag{3}$$

Moreover, the second measuring means 7 measures an external work volume $w_{2(i)}$ around each joint in accordance with the next equation (4) (FIG. 3 s5). That is, the external work volume $w_{2(i)}$ is measured by integrating the absolute value of the product of the external torque $T_{2(i)}$ around each joint and the angular velocity $\omega_{(i)}$ over the i-th period.

$$w_{2(i)} = \int dt \cdot |T_{2(i)} \times \omega_{(i)}| \tag{4}$$

It is to be noted that the internal torque $T_{1(i)}$, external torque $T_{2(i)}$, and angular velocity $\omega_{(i)}$ around each joint are physical amounts which are time functions fluctuating every moment even in the i-th period.

Furthermore, the reference work volume determining means 8 determines a reference work volume $w_{0(i+1)}$ of an i+1st period in accordance with the next equation (5) (FIG. 3 s6). In detail, first a fluctuation of a total work volume $w_{1(i)} + w_{2(i)}$ which is a sum of the internal work volume $w_{1(i)}$ and the external work volume $w_{2(i)}$ with respect to an internal work volume $w_{1(0)}$ at the time of the flatland walking measured beforehand is measured. That is, a reference work volume $w_{0(i+1)}$ is determined by subtracting a product of the second coefficient $c_2$ ($0 \leq c_2 \leq 1$) stored in the memory means 11 and a fluctuation $\Delta w_i$ from the total work volume $w_{1(i)} + w_{2(i)}$. The second coefficient c2 determines a ratio of a fluctuation compensated by an imparted external torque $T_{2(i+1)}$ in this fluctuation $\Delta w_i$. For example, when the second coefficient $c_2$ is set to 1.0, an external torque $T_{2(i+1)}$ is determined so as to compensate for all the fluctuations $\Delta w_i$, that is, so that the walking can be continued by the internal work volume $w_{1(0)}$ in a flatland walking state regardless of the fluctuation of a walking state. When the second coefficient $c_2$ is set to 0.5, the external torque $T_{2(i+1)}$ is determined so as to compensate for the half of the fluctuation $\Delta w_i$. It is to be noted that the second coefficient $c_2$ may also be set/updated in an operation panel (not shown) and the like.

$$w_{0(i+1)} = w_{1(i)} + w_{2(i)} - c_2 \Delta w_i \tag{5}$$

Moreover, the first coefficient determining means 9 determines a desired value $c_{TG(i+1)}$ of the first coefficient in accordance with the following equation (6) (FIG. 3 s7).

$$c_{TG(i+1)} = c_2 \Delta w_i / \{w_{1(0)} + (1-c_2)\Delta w_i\} \tag{6}$$

Moreover, the first coefficient determining means uses a gain coefficient G ($0 < G \leq 1$) stored in the memory means 11 to determine the first coefficient $c_{1(i+1)}$ in accordance with the following equation (7). The size of the gain coefficient G determines a speed at which the internal work volume $w_{1(i+1)}$ converges to the reference work volume $w_{0(i+1)}$. That is, the external torque $T_{2(i)}$ is increased so that the internal work volume $w_{1(i)}$ quickly converges to the reference work volume $w_{0(i)}$ with an increase of the gain coefficient G. It is to be noted that the gain coefficient G may also be set/updated in the operation panel (not shown).

$$c_{1(i+1)} = w_{2(i)}/w_{1(i)} + G(c_{TG(i+1)} - w_{2(i)}/w_{1(i)}) \tag{7}$$

Unless the operation of the walking assisting apparatus is ended (NO in s9 of FIG. 3), the first coefficient $c_{1(i)}$ of the i-th period is updated to $c_{1(i+1)}$ (FIG. 3 s11). Additionally, with respect to the i+1st period, the first measuring means 6 measures the internal torque $T_{1(i+1)}$ (FIG. 3 s1). Moreover, the external torque determining means 10 determines the external torque $T_{2(i+1)}$ as the product of the first coefficient $c_{1(i+1)}$ and the internal torque $T_{1(i+1)}$ as described above as in the following equation (8) (FIG. 3 s2).

$$T_{2(i+1)} = c_{1(i+1)} T_{1(i+1)} \tag{8}$$

Moreover, the external torque $T_{2(i+1)}$ determined by the external torque determining means 10 is imparted to the walker's leg body through the first and second actuators (FIG. 3 s2).

Figure 6:
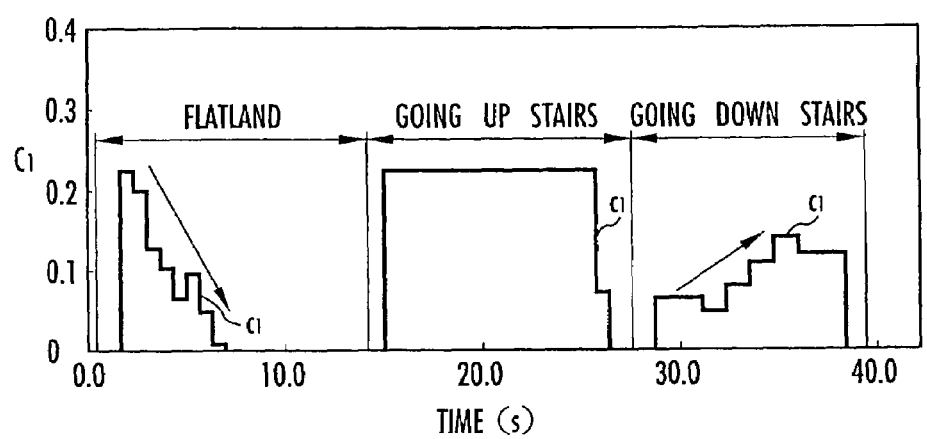
FIG. 6 is an explanatory view of an experiment result of the walking assistance by the walking assisting apparatus.

Next, a result of an experiment concerning the fluctuation of the external torque $T_2$ imparted to the walker's knee joint with the fluctuation of the walking conditions will be described with reference to FIG. 6. FIG. 6 shows the fluctuation of the first coefficient $c_1$ in a case in which the walker starts walking on the flatland, goes up the stairs, and goes down the stairs. As described above, since the first coefficient $c_1$ governs the percentage of the internal torque $T_1$ determined/imparted as the external torque $T_2$, the fluctuation of the external torque $T_2$ can indirectly be grasped through the fluctuation thereof. It is to be noted that in the experiment, an upper limit of the first coefficient $c_1$ is set to 0.25, and that of the second coefficient $c_2$ is set to 0.25.

At the time of the walking on the flatland, the first coefficient $c_1$ starting from 0 reaches the upper limit of 0.25, and thereafter gradually decreases to reach 0 (see downward arrows in the drawing). This indicates that immediately after the start of the walking on the flatland, a large external torque is imparted to the knee joint to assist the walker in walking, thereafter the external torque gradually decreases, and the walker walks on one's own.

Moreover, when the walker goes up the stairs, the first coefficient $c_1$ reaches the upper limit of 0.25 from 0, and is thereafter maintained at the upper limit substantially over the whole time. This indicates that while the walker goes up the stairs, the walker is assisted in walking by a steadily imparted large external torque to the knee joint thereof.

Furthermore, when the walker goes down the stairs, the first coefficient $c_1$ rises to about 0.1 from 0, slightly decreases, and gradually increases to about 0.15 (see upward arrows in the drawing). This indicates that a suitable external torque in going down the stairs, which is smaller than that in going up the stairs, is imparted to the knee joint to assist the walker in walking.

Figure 7:
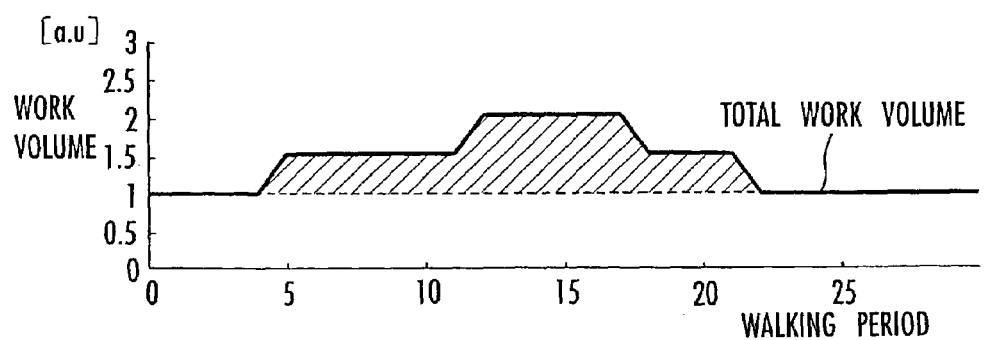

Subsequently, a result of simulation on the fluctuation of the external work volume $w_2$ imparted to the walker in relation to the fluctuation of the walking conditions will be described with reference to FIGS. 7 and 8. In FIGS. 7 and 8, the ordinate indicates the total work volume required for the walking, and the abscissa indicates a walking period of the walker. The work volume is standardized by the total work volume (dotted line) at the time of the flatland walking. Furthermore, in FIG. 7, the fluctuation of the total work volume on the basis of the volume at the time of the flatland walking is shown by slanted lines, and in FIG. 8, the fluctuation of the external work volume is shown by the slanted lines.

As shown in FIG. 7, it is assumed that the total work volume increases to 1.0 in first to fourth periods, to 1.5 from 1.0 in a fifth period, to 1.5 in sixth to eleventh periods, and to 2.0 from 1.5 in a twelfth period. The volume is maintained at 2.0 in a thirteenth to seventeenth periods, decreases to 1.5 from 2.0 in an eighteenth period, is maintained at 1.5 in a nineteenth to 21st periods, decreases to 1.0 from 1.5 in a 22nd period, and is maintained at 1.0 in and after a 23rd period. The increase of the total work volume follows, for example, a shift to the walking up the slope or stairs from the walking on the flatland, and the decrease of the total work volume follows, for example, the shift to the walking on the flatland from the walking up the slope or stairs.

The simulation results of the fluctuations of the internal and external work volumes are shown in FIGS. 8(a), 8(b), 8(c), and 8(d) in a case where combinations of the second coefficient $c_2$ and the gain coefficient G are assumed to be (1.0, 0.6), (0.5, 0.6), (1.0, 1.0), and (0.5, 1.0), respectively.

Referring to FIGS. 8(a) and 8(c), when the second coefficient $c_2$ is 1.0, the external torque and further the external work volume (shaded portions of FIGS. 8(a), 8(c)) imparted so as to compensate for all the fluctuation (shaded portions of FIG. 7) of the total work volume on the basis of that in the flatland walking state. Referring to FIGS. 8(b) and 8(d), when the second coefficient $c_2$ is 0.5, the external torque and further the external work volume (shaded portions of FIGS. 8(b), 8(d)) imparted so as to compensate for the half of the fluctuation (shaded portions of FIG. 7).

Moreover, in comparison of FIGS. 8(a) and 8(c), or FIGS. 8(b) and 8(d), it is apparent that when the gain coefficient G is large, the external torque imparted around the joint and further the external work volume (shaded portions of FIGS. 8(a) to 8(d)) quickly fluctuate in accordance with the fluctuation (shaded portions of FIG. 7). It is also apparent that when the gain coefficient G is small, the external work volume imparted around the joint (shaded portions of FIGS. 8(a) to 8(d)) moderately fluctuates in accordance with the fluctuation (shaded portions of FIG. 7). That is, as described above with reference to FIG. 2, the external work volume (whitened portion) $w_2$ gradually increases at the time of the walking-up of the stairs. However, when the gain coefficient G increases, a speed of the shift to FIG. 2 ② from ①, ③ from ②,④ from ③ increases. The smaller the gain coefficient G is, the lower the speed is.

According to the present walking assisting apparatus, the external torque $T_2$ around the joint is imparted to the leg body so that the internal work volume $w_1$ around the walker's joint of the leg body agrees with the reference work volume $w_0$. Therefore, when the walker shifts to the stairs walking from the flatland walking and the like, the walking conditions fluctuate, and the work volume of the leg body required for the walking exceeds the reference work volume $w_0$, the external torque $T_2$ is imparted to the leg bodies or the like in such a manner as to assist the surplus. Moreover, regardless of the fluctuation of the walking conditions, the walking is possible by the internal torque $T_1$ exerted in accordance with the reference work volume $w_0$ in the leg body.

Moreover, the external torque $T_2$ imparted to the leg body is determined on the basis of the first coefficient $c_1$ and further the external work volume $w_2$ imparted to the leg body (see the above equations (6) to (8)), and the reference work volume $w_0$ which is a reference in the determination is determined on the basis of the internal work volume $w_1$ of the leg body (see the above equation (5)). Therefore, the suitable external torque $T_2$ can be imparted to the leg body in accordance with a balance between the internal work volume w1 and the external work volume $w_2$ of the leg body.

Furthermore, when the gain coefficient G is increased, the convergence speed of the first coefficient $c_1$ to the desired value $c_{TG}$ can be increased. Moreover, when the work volume required for the walking exceeds the reference work volume $w_0$ by the fluctuation of the walking conditions, the external torque $T_2$ can be imparted to the leg body so as to quickly eliminate the surplus (see FIGS. 8(c), 8(d)). On the other hand, when the gain coefficient G is reduced, the convergence speed of the first coefficient $c_1$ to the desired value $c_{TG}$ can be reduced. Moreover, when the work volume required for the walking exceeds the reference work volume $w_0$ by the fluctuation of the walking conditions, the external torque $T_2$ can be imparted to the leg body so as to slowly eliminate the surplus (see FIGS. 8(a), 8(b)).

Moreover, for the fluctuation of the total work volume required for the walking with respect to the reference work volume $w_0$, the fluctuation to be compensated by the external torque $T_2$ is determined by the size of the second coefficient $c_2$. That is, when the second coefficient $c_2$ is set to be large, the ratio of the fluctuation to be compensated by the external torque $T_2$ in the fluctuations can be increased (see FIGS. 8(a), 8(c)). On the other hand, when the second coefficient $c_2$ is set to be small, the ratio of the fluctuation to be compensated by the external torque $T_2$ in the fluctuations can be reduced (see FIGS. 8(b), 8(d)).

It is to be noted that the external torque around the hip and knee joints is imparted to the walker's leg body in the present embodiment, but the external torque around the foot joint may also be imparted to the leg body in another embodiment, and an external torque of an arm around a hand root joint, elbow joint, or shoulder joint may also be imparted. That is, in the present embodiment, the "connected body" constituting an object to which the external torque is to be imparted includes the walker's waist and thigh connected through the hip joints, and the thigh and shin connected through the knee joints, but in the other embodiment, the "connected body" may also be the shin and foot connected through the foot joints.

Moreover, in the present embodiment, the external torque around the joint has been imparted to the leg body so as to assist the motion of a person, but in the other embodiment, the external torque around the joint may also be imparted to the leg body so as to assist the motions of animals such as cats and dogs. This means that the torque imparting system of the present invention can be applied not only to human medical care, welfare, and sport fields or the like but also to a field of veterinary medicine.

Furthermore, in the present embodiment, the external torque is imparted to the left/right leg bodies, but in the other embodiment, the external torque may be applied only to either one of left or right leg body.

In the present embodiment, the external torque $T_2$ has been imparted so as to assist the walker in walking, but in the other embodiment, the external torque $T_2$ may also be imparted in a direction reverse to a direction in which the walker is to move. According to the other embodiment, when the first coefficient determining means 9 determines the first coefficient $c_1$ to be negative, a symbol of the external torque $T_2$ differs from that of the internal torque $T_1$ (see the above equation (8)). Moreover, when the walker tries to move against the imparted external torque $T_2$, a walker's muscle force can be strengthened. That is, the torque imparting system of the present invention is used as a training apparatus for strengthening athletes' muscle forces or the like.

In the present embodiment, the control unit 3 is housed in the backpack 5 of the walking assisting apparatus, but in the other embodiment, the control unit 3 is separated from the walking assisting apparatus. By transmitting/receiving signals between the two, the internal torque $T_1$ in the control unit 3 may be measured, the external torque $T_2$ may be determined, or operation instructions of the first and second actuators 1, 2 may also be given.

Moreover, the first coefficient determining means 9 may determine the lower limit of the first coefficient $c_1$ as 0, when the total work volume as the sum of the internal work volume $w_1$ measured by the first measuring means 6 and the external work volume $w_2$ measured by the second measuring means 7 is equal to or less than the reference work volume $w_0$ determined by the reference work volume determining means 8. Accordingly, when the total work volume $w_1+w_2$ of the leg body decreases to be below the reference work volume $w_0$, a situation can be prevented in which the first coefficient $c_1$ is determined to be negative and the negative external torque $T_2$ is imparted to the leg body.

Furthermore, the first coefficient determining means 9 may also determine the upper limit of the first coefficient $c_1$, when the total work volume $w_1+w_2$ of the leg body is equal to or more than a predetermined volume ($0$, $1.5w_0$, $2.5w_0$, ... and the like) equal to or more than the reference work volume $w_0$ determined by the reference work volume determining means 8. Accordingly, when the total work volume $w_1+w_2$ of the leg body increases to largely exceed the reference work volume $w_0$, a situation can be prevented in which the first coefficient $c_1$ is determined to be excessively large and the excessively large external torque $T_2$ is imparted to the leg body.

In the present embodiment, the product of the internal torque $T_1$ and angular velocity $\omega_1$, and the product of the external torque $T_2$ and angular velocity $\omega_2$ are time-integrated over the walking period of the walker, and the internal work volume $w_1$ and external work volume $w_2$ are measured based on the integral time (see the above equations (3), (4), and s3 to s5 of FIG. 3), but in the other embodiment, the integral time may also be a unit time, and may also be a different time such as a time required for the walker to move by a unit distance.

In the present embodiment, the internal torque $T_1$ and internal work volume $w_1$ of the knee and hip joints have been measured on the basis of the floor reaction force onto the leg body in accordance with the inverse kinetic model (see FIG. 5, equations (2a) to (2c), and in the other embodiment, the internal torque $T_1$ and internal work volume $w_1$ of each joint may also be measured by a three-dimensional motion analysis apparatus. That is, the motion of the leg body is photographed from xyz directions, an image indicating an angle of each joint bent at an angular velocity $\omega_1$ is analyzed, and the internal torque $T_1$ or the internal work volume $w_1$ of each joint may be measured on the basis of this analysis result.

In the present embodiment, the floor reaction force onto the walker's leg body has been measured on the basis of the measured values of the angle sensors a and the like (see FIG. 4, equations (1a) to (1d)), but in the other embodiment, a floor reaction force sensor is disposed on walker's shoes, and accordingly the floor reaction force may directly be measured.

In the present embodiment, the internal torque $T_1$ and (internal) angular velocity $\omega$ around the joint are measured, and the absolute value of the product of the both is time-integrated to measure the internal work volume $w_1$ around the joint (see the equation (3)). In the other embodiment, muscle shrinkage force and speed associated with the walker's joint are measured, and the internal work volume $w_1$ around the joint may also be measured on the basis of the product of the both. Alternatively, the angle of left/right thighs, shin and the like to the vertical direction, or the movement distances of the feet are measured, a correspondence data table of the measured value and the internal work volume $w_1$ is stored/held by the memory means 11, and the measured value and data table may be used to measure the internal work volume $w_1$.

In the present embodiment, the external torque $T_2$ and (external) angular velocity $\omega$ around the joint are measured, the absolute value of the product of the both is time-integrated, and accordingly the external work volume $w_2$ around the joint is measured (see the equation (4)). However, in the other embodiment, power consumptions of the respective actuators 1, 2 are measured, and the external work volume $w_2$ may also be measured on the basis of the power consumption. When the actuators 1, 2 are of a hydraulic type, the fluctuation of a hydraulic pressure is measured, then the external work volume $w_2$ may also be measured on the basis of the integral time of the hydraulic pressure fluctuation.

Here, still another embodiment of the present invention will be described. The product of the external torque $T_2$ around the walker's joint and the angular velocity $\omega$ thereof in the case where the walker walks up the stairs is considered. It is assumed that a direction for bending the knees is "negative", and a stretching direction is "positive".

When a walker's stepped right foot contacts an upper stair, the right knee bends. Next, when the walker detaches the left foot from a lower stair so as to walk up the stairs, the "positive" internal torque $T_1$ is generated so that the right knee is stretched from a bent state so as to lift up the walker's body. Moreover, the actuator 2 (see FIG. 1) attached to the right knee imparts the "positive" external torque $T_2$ so as to assist the right knee in stretching. However, immediately after the walker detaches the left foot from the lower stair, the right knee slightly bends by a walker's body weight, and the angular velocity $\omega$ becomes "negative". Therefore, both the product of the internal torque $T_1$ and the angular velocity $\omega$, and the product of the external torque $T_2$ and the angular velocity $\omega$ are both "negative".

Subsequently, with an elapse of a certain degree of time from when the walker detaches the left foot, the walker's right knee gradually stretches from the bent state by the "positive" internal torque T1 and external torque $T_2$, and the angular velocity $\omega$ becomes "positive". Therefore, both the product of the internal torque $T_1$ and angular velocity $\omega$ and the product of the external torque $T_2$ and angular velocity $\omega$ are "positive".

As seen from above, there may be cases where the product of the torque and angular velocity is sometimes "positive" or "negative" even in one walking period depending on the walking conditions.

To handle such situations, in the other embodiment, the first measuring means 6 and second measuring means 7 measure integrated portions $w_{1(i)}^+$, $w_{2(i)}^+$ with the positive product of the internal and external work volumes $w_{1(i)}$, $w_{2(i)}$ in accordance with the following equations (9) to (12), and integrated portions $w_{1(i)}^-$, $w_{2(i)}^-$ with the negative product thereof in a divided manner.

$$w_{1(i)} = w_{1(i)}^+ + w_{1(i)}^- \qquad (9)$$
$$= \int dt \circ f^+(T_{1(i)} \times \omega_{(i)}) +$$
$$\int dt \circ f^-(T_{1(i)} \times \omega_{(i)})$$

-continued $$w_{2(i)} = w_{2(i)}^+ + w_{2(i)}^- \quad (10)$$
$$= \int dt \circ f^+(T_{2(i)} \times \omega_{(i)}) +$$
$$\int dt \circ f^-(T_{2(i)} \times \omega_{(i)})$$

$$f^+(x) \approx x (\text{if } x \geq 0), 0 (\text{if } x<0) \quad (11)$$

$$f^-(x) \approx 0 (\text{if } x \geq 0), -x (\text{if } x<0) \quad (12)$$

Additionally, the first coefficient determining means 9 determines different first coefficients $c_{1(i+1)}^+$, $c_{1(i+1)}^-$ on the basis of $w_{1(i)}^+$ and $w_{2(i)}^+$, further $w_{1(i)}^-$ and $w_{2(i)}^-$ (see the equation (7)).

Moreover, the external torque determining means 10 determines the external torque $T_{2(i+1)}$ on the basis of the first coefficient $c_{1(i+1)}^+$ determined in accordance with the "positive" product in the i-th period, when the product of the internal torque $T_{1(i+1)}$ and the angular velocity $\omega_{(i+1)}$ is "positive" in an i+1st period (see the equation (8)). On the other hand, the external torque $T_{2(i+1)}$ is determined on the basis of the first coefficient $c_{1(i+1)}^-$ determined in accordance with the "negative" product in the i-th period, when the product is "negative" (the same as above).

Therefore, with the walking conditions agreeing with the past walking conditions, the existing external torque $T_2$ can be determined/imparted on the basis of the first coefficient $c_1$ determined beforehand in accordance with the past walking conditions.

Moreover, in the other embodiment, the first coefficient $c_1$ and further the external torque $T_2$ have been determined depending on whether the product of the internal torque $T_1$ and angular velocity $\omega$ is positive/negative, but in still another embodiment, the first coefficient $c_1$ may also be determined in accordance with three or more segments of the product. For example, the first coefficient $c_1$ may also be determined, when the product is less than −2, not less than −2 and less than +1, or +1 or more by an arbitrary unit.

The invention claimed is:

1. A system for imparting an external torque around at least one joint of a connected body, wherein the connected body is a living thing or a living portion of the living thing, and wherein the system is relatively and rotatably connected to the at least one joint of the connected body, the system comprising:
    a first measuring means for measuring an internal work volume based upon an internal torque around the at least one joint of the connected body as the connected body rotates the at least one joint;
    a second measuring means for measuring an external work volume based upon the external torque imparted to the at least one joint of the connected body;
    a reference work volume determining means for determining a reference work volume on a first basis of the internal work volume of the connected body measured by the first measuring means;
    an external torque determining means for determining the external torque to be imparted to the connected body such that a sum of the internal work volume and the external work volume approaches and substantially equals the reference work volume determined by the reference work volume determining means, wherein the external torque to be imparted to the connected body is determined on a second basis of the external work volume measured by the second measuring means; and
    a movement assisting apparatus for imparting the external torque to the connected body and adjusting the imparted external torque to the connected body such that the imparted external torque remains equal to the determined external torque that is determined by the external torque determining means;
    wherein the movement assisting apparatus comprises at least one actuator and attaching elements attached to the connected body at both sides of the at least one joint;
    wherein the internal work volume is a work volume achieved by a voluntary movement of the connected body, and the external work volume is a work volume achieved by a force imparted from the at least one actuator via the attaching elements to the connected body, which is independent from the connected body and is included in the system for imparting the external torque to be fixed to the connected body.

2. The torque imparting system according to claim 1, wherein the connected body is a walker's leg body including a hip joint, knee joint, and foot joint.

3. The torque imparting system according to claim 2, further comprising:
    a first coefficient determining means for regarding a ratio of the external work volume imparted to the connected body with respect to the internal work volume of the connected body as a desired value in a case in which a difference from the reference work volume determined by the reference work volume determining means is 0 and for successively determining a first coefficient so that the coefficient converges to the desired value with an elapse of time, wherein the first measuring means measures the internal torque around the joint of the connected body,
    the external torque determining means calculates a product of the internal torque of the connected body measured by the first measuring means and the first coefficient determined by the first coefficient determining means, and
    a calculation result is determined as the external torque imparted to the connected body.

4. The torque imparting system according to claim 3, wherein the first coefficient determining means determines an upper limit or a lower limit of the first coefficient on the first basis of the internal work volume measured by the first measuring means or the second basis of the external work volume measured by the second measuring means.

5. The torque imparting system according to claim 3, wherein the first coefficient determining means determines the lower limit of the first coefficient as 0, when a total work volume that is a sum of the internal work volume determined by the first measuring means and the external work volume measured by the second measuring means is not more than the reference work volume determined by the reference work volume determining means.

6. The torque imparting system according to claim 3, wherein the first coefficient determining means determines the upper limit of the first coefficient, when the total work volume that is the sum of the internal work volume determined by the first measuring means and the external work volume measured by the second measuring means is not less than a predetermined volume not less than the reference work volume determined by the reference work volume determining means.

7. The torque imparting system according to claim 3, wherein the first measuring means measures a product of the internal torque of the connected body around the joint and an angular velocity thereof, the first coefficient determining means segments and determines the first coefficient in accordance with a segment of the product measured by the first measuring means, and the external torque determining means uses the first coefficient previously determined on the basis of the internal work volume in accordance with a past segment of the product by the first coefficient determining means to determine the external torque, when the segment of the product measured by the first measuring means agrees with the past segment of the product previously measured by the first measuring means.

8. The torque imparting system according to claim 7, wherein the first coefficient determining means segments and determines the first coefficient depending on whether the product of the internal torque of the connected body around the joint measured by the first measuring means and the angular velocity is positive or negative.

9. The torque imparting system according to claim 3, wherein the reference work volume determining means calculates a total work volume which is a sum of the internal work volume measured by the first measuring means and the external work volume measured by the second measuring means, a product of a difference between the total work volume and the internal work volume of the connected body in a non-load state measured by the first measuring means, and a second coefficient concerning the external torque assuming that the difference between the internal work volume of the connected body and the reference work volume is 0 is calculated, and a difference between the total work volume and the product is calculated to determine the calculation result as the reference work volume.

10. The torque imparting system according to claim 3, wherein the first and second measuring means regard a motion period of the connected body as an integration time to measure the internal and external work volumes.

11. The torque imparting system according to claim 3, wherein the first measuring means measures a reaction force which works on one joint of the connected body, measures a total torque of the internal torque and external torque of the connected body around each joint in accordance with an inverse kinetic model on the basis of the measured reaction force, and calculates a difference from the external torque measured by the second measuring means from the measured total torque to measure the internal torque of the connected body around each joint.

12. The torque imparting system according to claim 2, wherein the reference work volume determining means calculates a total work volume which is a sum of the internal work volume measured by the first measuring means and the external work volume measured by the second measuring means, a product of a difference between the total work volume and the internal work volume of the connected body in a non-load state measured by the first measuring means, and a second coefficient concerning the external torque assuming that the difference between the internal work volume of the connected body and the reference work volume is 0 is calculated, and a difference between the total work volume and the product is calculated to determine the calculation result as the reference work volume.

13. The torque imparting system according to claim 2, wherein the first and second measuring means regard a motion period of the connected body as an integration time to measure the internal and external work volumes.

14. The torque imparting system according to claim 2, wherein the first measuring means measures a reaction force which works on one joint of the connected body, measures a total torque of the internal torque and external torque of the connected body around each joint in accordance with an inverse kinetic model on the basis of the measured reaction force, and calculates a difference from the external torque measured by the second measuring means from the measured total torque to measure the internal torque of the connected body around each joint.

15. The torque imparting system according to claim 1, further comprising:

a first coefficient determining means for regarding a ratio of the external work volume imparted to the connected body with respect to the internal work volume of the connected body as a desired value in a case in which a difference from the reference work volume determined by the reference work volume determining means is 0 and for successively determining a first coefficient so that the coefficient converges to the desired value with an elapse of time, wherein the first measuring means measures the internal torque around the joint of the connected body, the external torque determining means calculates a product of the internal torque of the connected body measured by the first measuring means and the first coefficient determined by the first coefficient determining means, and a calculation result is determined as the external torque imparted to the connected body.

16. The torque imparting system according to claim 15, wherein the first coefficient determining means determines an upper limit or a lower limit of the first coefficient on the first basis of the internal work volume measured by the first measuring means or the second basis of the external work volume measured by the second measuring means.

17. The torque imparting system according to claim 15, wherein the first coefficient determining means determines the lower limit of the first coefficient as 0, when a total work volume that is a sum of the internal work volume determined by the first measuring means and the external work volume measured by the second measuring means is not more than the reference work volume determined by the reference work volume determining means.

18. The torque imparting system according to claim 15, wherein the first coefficient determining means determines the upper limit of the first coefficient, when the total work volume that is the sum of the internal work volume determined by the first measuring means and the external work volume measured by the second measuring means is not less than a predetermined volume not less than the reference work volume determined by the reference work volume determining means.

19. The torque imparting system according to claim 15, wherein the first measuring means measures a product of the internal torque of the connected body around the joint and an angular velocity thereof, the first coefficient determining means segments and determines the first coefficient in accordance with a segment of the product measured by the first measuring means, and the external torque determining means uses the first coefficient previously determined on the basis of the internal work volume in accordance with a past segment of the product by the first coefficient determining means to determine the external torque, when the segment of the product measured by the first measuring means agrees with the past segment of the product previously measured by the first measuring means.

20. The torque imparting system according to claim 19, wherein the first coefficient determining means segments and determines the first coefficient depending on whether the product of the internal torque of the connected body around the joint measured by the first measuring means and the angular velocity is positive or negative.

21. The torque imparting system according to claim 15, wherein the reference work volume determining means calculates a total work volume which is a sum of the internal work volume measured by the first measuring means and the external work volume measured by the second measuring means,
a product of a difference between the total work volume and the internal work volume of the connected body in a non-load state measured by the first measuring means, and a second coefficient concerning the external torque assuming that the difference between the internal work volume of the connected body and the reference work volume is 0 is calculated, and
a difference between the total work volume and the product is calculated to determine the calculation result as the reference work volume.

22. The torque imparting system according to claim 15, wherein the first and second measuring means regard a motion period of the connected body as an integration time to measure the internal and external work volumes.

23. The torque imparting system according to claim 15, wherein the first measuring means measures a reaction force which works on one joint of the connected body, measures a total torque of the internal torque and external torque of the connected body around each joint in accordance with an inverse kinetic model on the basis of the measured reaction force, and calculates a difference from the external torque measured by the second measuring means from the measured total torque to measure the internal torque of the connected body around each joint.

24. The torque imparting system according to claim 1, wherein the reference work volume determining means calculates a total work volume which is a sum of the internal work volume measured by the first measuring means and the external work volume measured by the second measuring means,
a product of a difference between the total work volume and the internal work volume of the connected body in a non-load state measured by the first measuring means, and a second coefficient concerning the external torque assuming that the difference between the internal work volume of the connected body and the reference work volume is 0 is calculated, and
a difference between the total work volume and the product is calculated to determine the calculation result as the reference work volume.

25. The torque imparting system according to claim 1, wherein the first and second measuring means regard a motion period of the connected body as an integration time to measure the internal and external work volumes.

26. The torque imparting system according to claim 1, wherein the first measuring means measures a reaction force which works on one joint of the connected body, measures a total torque of the internal torque and external torque of the connected body around each joint in accordance with an inverse kinetic model on the basis of the measured reaction force, and calculates a difference from the external torque measured by the second measuring means from the measured total torque to measure the internal torque of the connected body around each joint.

27. The torque imparting system according to claim 1, wherein the movement assisting apparatus is adapted to be connected to the connected body, wherein the connected body is a human being, and the first measuring means for measuring the internal work volume measures the muscle strength of the human being.

28. The torque imparting system according to claim 1, wherein
the first measuring means and the second measuring means continuously measure the internal and external work volumes;
the reference work volume determining means continuously determines the reference work volume such that the reference work volume changes in response to changes in the measured internal work volume;
the external torque determining means continuously determines the external torque to be imparted to the connected body in response to changes in the internal work volume and the reference work volume; and
the movement assisting apparatus continuously adjusts the external torque imparted to the connected body in response to changes in the determined external torque.

29. The torque imparting system according to claim 28, wherein the external torque determining means determines the external torque to be imparted to the connected body while the sum of the internal work and the external work volume is unequal to the reference work volume; and
the movement assisting apparatus adjusts the external torque to be applied to the connected body when the determined external torque changes.

* * * * *